(12) United States Patent
Fukumori et al.

(10) Patent No.: US 7,016,043 B2
(45) Date of Patent: Mar. 21, 2006

(54) QUALITY EVALUATION METHOD AND APPARATUS FOR NON-BRAN RICE

(75) Inventors: Takeshi Fukumori, Tokyo (JP);
Shigeharu Kanemoto, Tokyo (JP);
Nobuhiro Matsumoto, Tokyo (JP);
Takamasa Mesaki, Tokyo (JP);
Hiroyuki Maehara, Tokyo (JP); Yuka Kuribayashi, Tokyo (JP); Michiko Matsuda, Tokyo (JP); Kazuo Amano, Tokyo (JP)

(73) Assignees: Satake Corporation, Tokyo (JP);
Japan Rice Millers Association, Tokyo (JP)

( * ) Notice: Subject to any disclaimer, the term of this patent is extended or adjusted under 35 U.S.C. 154(b) by 276 days.

(21) Appl. No.: 10/270,501

(22) Filed: Oct. 16, 2002

(65) Prior Publication Data

US 2003/0112440 A1    Jun. 19, 2003

(30) Foreign Application Priority Data

Oct. 31, 2001    (JP)    .............................. 2001-335199

(51) Int. Cl.
*G01N 21/00*    (2006.01)
*G01N 21/64*    (2006.01)
*B07C 5/01*    (2006.01)

(52) U.S. Cl. ................ 356/432; 250/461.2; 250/458.1; 209/558; 209/580; 426/231

(58) Field of Classification Search ........ 356/432–435, 356/237.1, 239.1; 250/221, 221.1, 223 R, 250/461.2, 341.6, 458.1; 209/580, 587, 557, 209/558; 426/231

See application file for complete search history.

(56) References Cited

U.S. PATENT DOCUMENTS

| | | | | |
|---|---|---|---|---|
| 4,421,772 A * | 12/1983 | Munck et al. | ............... | 426/231 |
| 4,866,283 A * | 9/1989 | Hill, Jr. | ................... | 250/461.2 |
| 5,135,114 A * | 8/1992 | Satake et al. | ............... | 209/558 |
| 6,097,493 A * | 8/2000 | Satake et al. | ............... | 356/609 |
| 6,225,620 B1 * | 5/2001 | Campbell et al. | ........... | 250/221 |
| 6,271,520 B1 * | 8/2001 | Tao et al. | .................... | 250/330 |
| 6,391,354 B1 * | 5/2002 | Shibayama et al. | ......... | 426/231 |
| 6,427,128 B1 * | 7/2002 | Satake et al. | ................. | 702/81 |
| 6,563,122 B1 * | 5/2003 | Ludeker et al. | .......... | 250/458.1 |

FOREIGN PATENT DOCUMENTS

| | | | | |
|---|---|---|---|---|
| JP | 04350544 A | * | 12/1992 | |
| JP | 05133883 A | * | 5/1993 | |
| JP | 05149873 A | * | 6/1993 | |

* cited by examiner

Primary Examiner—Gregory J. Toatley, Jr.
Assistant Examiner—Sang H. Nguyen
(74) Attorney, Agent, or Firm—Staas & Halsey LLP

(57) ABSTRACT

A quality evaluation method and apparatus for non-bran rice evaluate quality or taste of non-bran rice by identifying proportions of a hull layer, an aleurone layer, an endosperm layer, which adhere to a surface of the non-bran rice according to luminance levels of self-emitted fluorescence obtained by irradiating the non-bran rice with excitation light.

11 Claims, 7 Drawing Sheets

ADHERENCE PROPORTION OF HULL LAYER

A  LIGHTLY PROCESSED TYPE
    OF NON-BRAN RICE

B  MEDIUM PROCESSED TYPE
    OF NON-BRAN RICE

C  HEAVILY PROCESSED TYPE
    OF NON-BRAN RICE

QUALITY EVALUATION METHOD AND APPARATUS FOR NON-BRAN RICE

BACKGROUND OF THE INVENTION

1. Field of the Invention

The present invention relates to a quality evaluation method and apparatus for non-bran rice, for evaluating the quality of non-bran rice products that are made by performing non-bran processing for polished rice after being hulled.

2. Description of the Related Art

So-called non-bran rice that can be cooked without being washed before cooking has been conventionally known. As for a production method of the non-bran rice, the method for removing rice bran powders and aleurone layer adhering to polished rice by hulling in the water, the method for adsorbing and removing the rice bran powders and aleurone layer adhering to polished rice with a cohesive substance, and the method for removing rice bran powders and aleurone layer by polishing polished rice with a dry method, are known. The non-bran rice produced by such processes is required to be conveniently cooked without before-cook washing, and also to have further added quality such as good taste and excellent storage properties. The turbidity when shaking and mixing the products immersed in water, whiteness of the products, water content, fatty acid content, water immersion broken grain rate of the products and the like are taken as the evaluation items so far in order to determine the quality of the products.

For example, as for the turbidity, the evaluation is carried out according to the method comprising the steps of putting non-bran rice sample of 20 g into an Erlenmeyer flask, closing it with a rubber stopper after water of 200 ml is poured, shaking it for ten minutes (144 to 150 cycles/minute, speed scale 3.5) with a shaking machine (made by Yamato Scientific Co., Ltd., Shaking machine, the model SA-31A), and measuring the diluted solution thereof with a turbidimeter (made by Nodal Communications Co., Ltd., Turbidimeter, the model M-204). It is generally considered desirable as non-bran rice if the measured value with the turbidimeter is 80 ppm or less.

However, with the above-described evaluation items such as turbidity, whiteness, water content, fatty acid content, and water immersion broken grain rate, the same evaluation items as used for the polished rice before non-bran rice processing are applied to the non-bran rice, and thus it is not possible to discriminate a test a layer, a Prichard layer and an aleurone layer, which constitute a very small amount of rice bran ingredients adhering to the surface of the non-bran rice to be a product, from an endosperm layer. Since the evaluation method of non-bran rice which makes it possible to identify a very small amount of rice bran ingredients is not established as described above, an evaluation and measuring apparatus exclusive for non-bran rice does not exist as an inevitable consequence. It is considered to perform point rating for each non-bran rice by means of taste evaluation apparatuses which are widely used in rice polishing factories and the like, but it is actually the point rating of the types and brands of polished rice and taste by sensory testing. Thus it is difficult to evaluate the quality of non-bran rice of which processing yield and surface condition are different from polished rice.

Incidentally, it is conventionally known that the compositions of protein and starch are identified by utilizing fluorescence emission. For example, U.S. Pat. No. 4,421,772 discloses a method which makes it possible to identify a hull layer, an aleurone layer, and starchy endosperm part of a grain with reliability. According to the method, it is characterized by including, in the method for identifying the component proportions in the grain product made by crushing, the step of irradiating electromagnetic radiation rays in the wavelength range of about 250 to about 300 nm to excite a starchy endosperm part in the product to emit fluorescence, irradiating electromagnetic radiation rays in the wavelength range of about 300 to about 370 nm to excite an aleurone layer part in the product to emit fluorescence, and further irradiating electromagnetic radiation rays in the wavelength range of about 410 to about 490 nm to excite a hull layer part in the product to emit fluorescence, and the step of analyzing the resultant fluorescence emitted by the product to identify the relative component proportions of the starchy endosperm, the aleurone layer and the hull layer in the product.

Meanwhile, U.S. Pat. No. 4,713,781 discloses a grain damage measuring system for identifying a damaged part and a part not damaged by illuminating a grain sample with a lamp of electromagnetic radiation in a selected wavelength range, causing the exposed starch part of the grain to fluoresce, and thereby causing visual contrast between the damaged part and the part not damaged of the grain sample.

However, the grain component identifying method disclosed in U.S. Pat. No. 4,421,772 is a technique of irradiating the starchy endosperm part, aleurone layer part and hull layer part with peculiar excitation wavelength suitable to the respective regions, and combining the fluorescence emissions separately measured into the entire grain, and therefore it has the disadvantage that the spot, where the area of the aleurone layer part and the area of the hull layer part overlap, occurs (excitation overlapping phenomenon), and accurate component analysis cannot be made.

In the grain damage measuring system disclosed in U.S. Pat. No. 4,713,781, it can be only determined whether or not the grain is damaged, and therefore this is not used for component analysis of a grain. Further, in both of the Patents, each of the ingredients of the grain is not related to a sensory value such as taste, while in the conventional taste evaluation apparatus, influence of a very small amount of rice bran adhering to the non-bran rice surface on taste is not considered, and thus detailed analysis of taste evaluation for non-bran rice cannot be made.

SUMMARY OF THE INVENTION

The present invention has its object to provide a quality evaluation method and apparatus for non-bran rice which are capable of performing accurate ingredient analysis, sensory evaluation such as taste, and ranking of non-bran rice.

In order to attain the above-described object, the present invention is a method for performing quality evaluation of non-bran rice products which are made by performing non-bran processing for polished rice after hulling, and takes a technical measure of evaluating quality by simultaneously identifying a quantitative proportion of each of parts of a hull layer (including test a layer and Prichard layer), an aleurone layer and an endosperm layer, which adhere to the surface, according to a difference in luminance of self-emitted fluorescence obtained by irradiating objects to be measured (measurement objects) with excitation light.

According to the invention, concerning non-bran rice products made by performing non-bran processing of polished rice after hulling, it is made possible to evaluate the quality by simultaneously identifying the quantitative proportion of each of the parts of the hull layer, the aleurone layer and the endosperm layer adhering to the surface, and dividing the non-bran rice being the measurement objects into three groups: the lightly-processed non-bran rice which is cooked to be more delicious when the product is washed about twice to three times before being cooked, the medium-processed non-bran rice which is cooked to be more delicious when the product is washed once before being cooked, and the heavily-processed non-bran rice which can be cooked without washing the product before being cooked to evaluate the quality.

Since the luminance of the self-emitted fluorescence is obtained by utilizing transmission light or reflection light that is obtained by irradiating the measurement objects with excitation light, the inside condition other than the surface condition of the measurement objects can also be optically evaluated as compared with the method for performing measurement with only reflection light or transmission light.

Further, since light with a wavelength in a green range of about 560 to 570 nm is irradiated to the measurement objects as the excitation light and a wavelength in a red range of about 590 nm or more is obtained from the measurement objects as self-emitted fluorescence, self-emitted fluorescence in a visible light beam range can be obtained, and the quantitative proportion of each of the parts of the hull layer, aleurone layer and endosperm layer, which adhere to the surface, can be visually grasped by simple image means such as a monitor.

Since the quantitative proportion of each of the parts of the hull layer, aleurone layer and endosperm layer is simultaneously identified and taste of the non-bran rice is evaluated, and displayed, taste evaluation for non-bran rice can be analyzed in detail by linking the correlation of the quantitative proportion of each of the parts and sensory values such as a taste value.

An apparatus for performing quality evaluation of non-bran rice products includes an excitation light source for irradiating measurement objects with excitation light, measurement object holding means for holding the measurement objects at a measurement position, light receiver means for obtaining luminance of self-emitted fluorescence obtained from transmission light or reflection light from the measurement objects, arithmetic operation and control means for calculating a quantitative proportion of each of parts of a hull layer, an aleurone layer and an endosperm layer, which adhere to surfaces of the measurement objects, and calculating quality or a taste value of the non-bran rice, and display means for displaying values arithmetically operated with the arithmetic operation and control means, and therefore the quality evaluation apparatus for the non-bran rice can be provided by means of the simple optical device.

Since light-emitting diode is used as the excitation light source, and a CCD line sensor or a CMOS line sensor is used as the light receiver means, the quality evaluation apparatus for the non-bran rice can be provided by means of a compact optical device at low price.

Since the light-emitting diode used as the excitation light source uses a ring-shaped light source comprising a plurality of elements, the entire measurement objects held by the measurement object holding means can be irradiated with the excitation light without unevenness.

Since the measurement object holding means has a slide plate structure which moves the measurement objects to a supply position, the measurement position and a discharge position, the measurement object holding means is formed of a transparent material which transmits light beams from the excitation light source, and is provided with a plurality of rows of groove portions so as to align the measurement objects in a plurality of rows in a single layer state, supply of the measurement objects to the measurement object holding means, transfer of them to the measurement position, and discharge of the measurement objects from the measurement object holding means can be continuously performed, quality evaluation is performed more accurately by measuring the front portion and the reverse portion of the measurement objects, and the measurement objects are aligned in the single layer state in which two of the objects do not overlap each other, thereby making it possible to obtain a clear image.

Further, since the display means comprises an ingredient display section for displaying the proportion of each of the parts of the hull layer, the aleurone layer and the endosperm layer, and a quality evaluation display section for displaying the quality or the taste value of the non-bran rice in points or ranking, the proportion of each of the parts of the hull layer, aleurone layer, and endosperm layer is displayed and the quality evaluation of the non-bran rice can be understood more precisely, as compared with the apparatus which displays only the quality or the taste value of the non-bran rice in points and ranking.

DETAILED DESCRIPTION OF THE PREFERRED EMBODIMENTS

Figure 6:
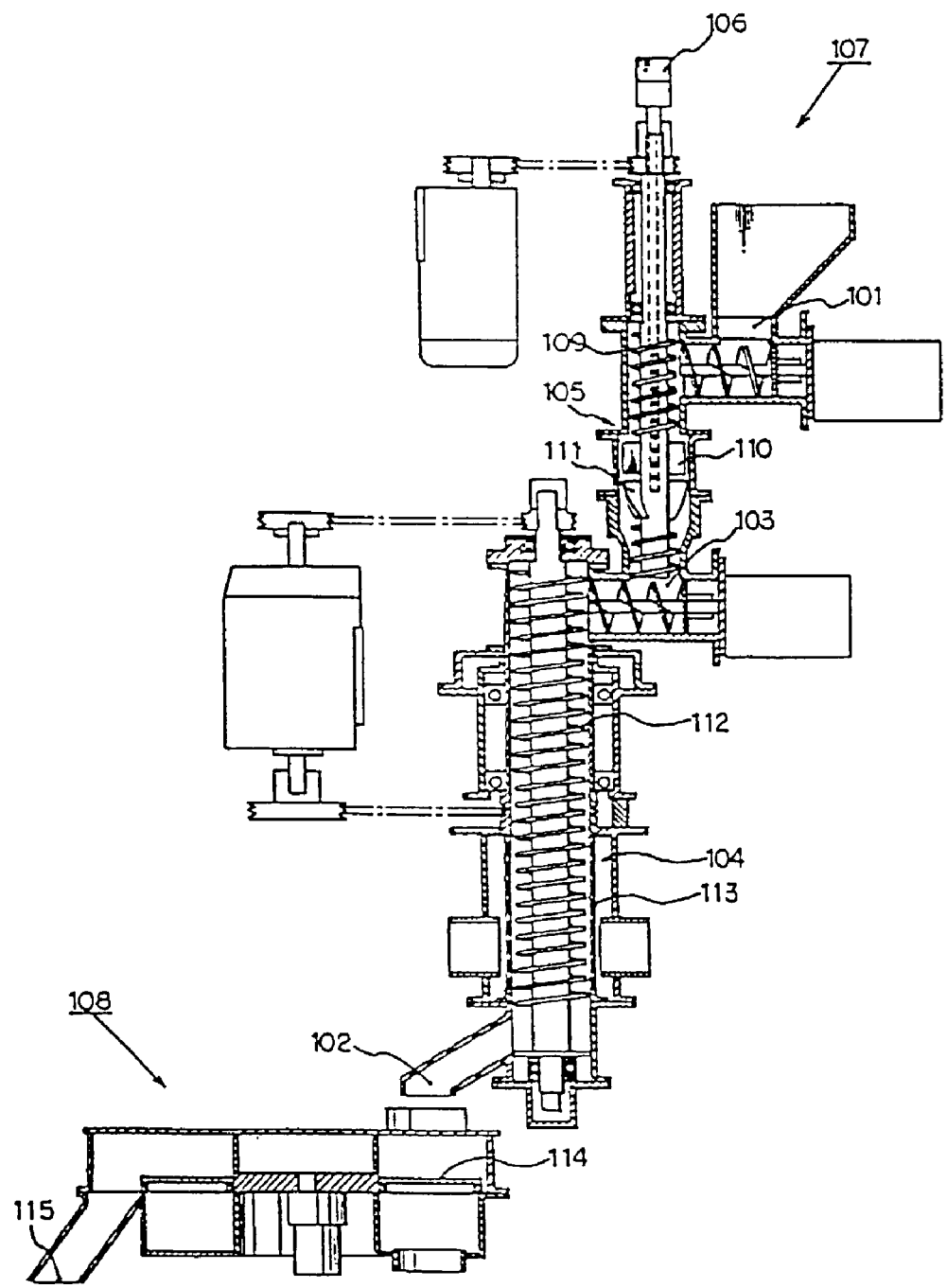
FIG. 6 is a longitudinal sectional view showing a schematic structure of a non-bran rice production apparatus.
Figure 7:
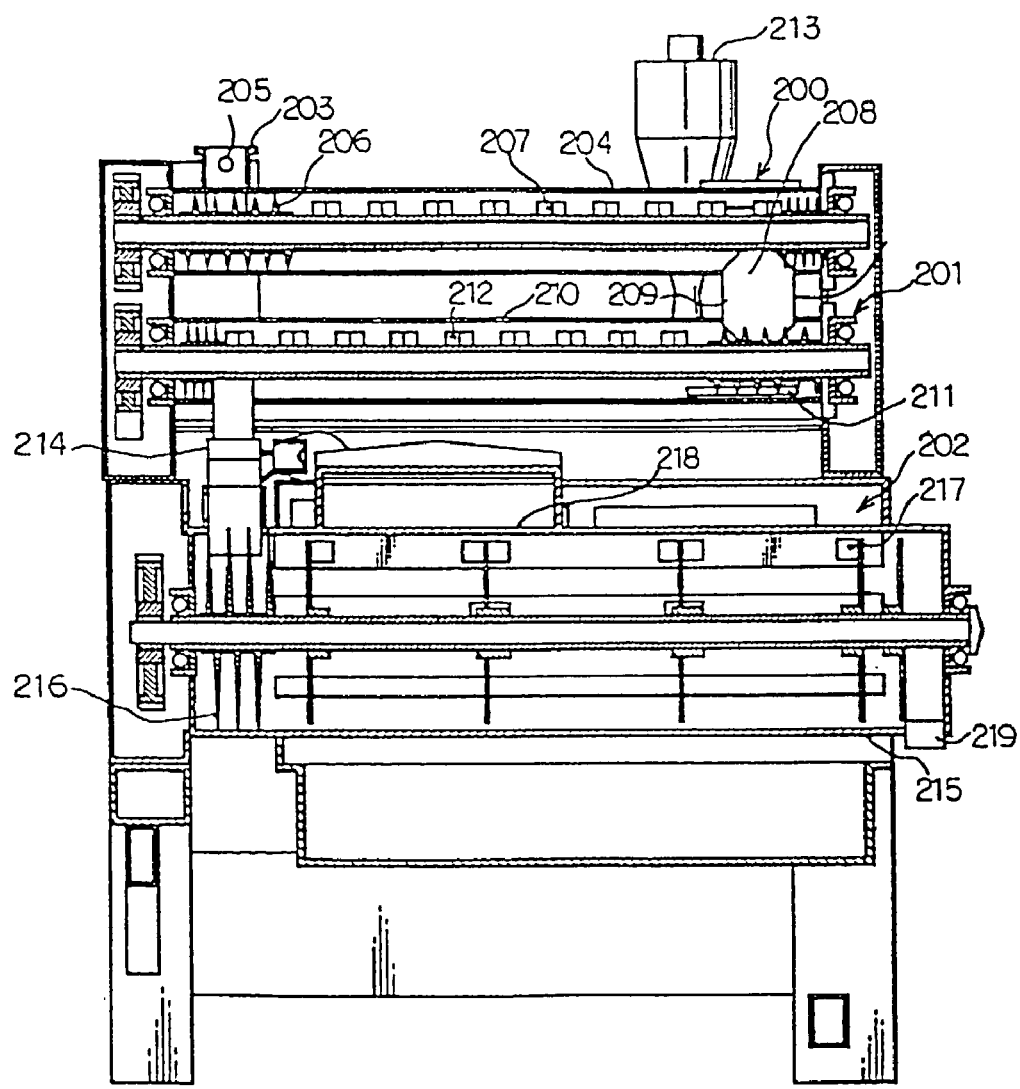
FIG. 7 is a longitudinal sectional view showing a schematic structure of a non-bran rice production apparatus.

First of all, as the production method of non-bran rice, there are the methods using, for example, a non-bran rice production apparatus A which removes rice bran powders and an aleurone layer adhereing to polished rice after hulling by hulling in water, as shown in FIG. 6, and using a non-bran rice production apparatus B which adsorbs and removes rice bran powders and an aleurone layer adhering to polished rice with a cohesive substance, as shown in FIG. 7.

With reference to FIG. 6, the non-bran rice production apparatus A (refer to Japanese Patent Application Laid-Open No. 11-42056) is composed of a hulling device 107 and a moisture conditioning device 108. In the hulling device 107, a polished rice supply section 101 is provided at one end, and a discharge section 102 is provided at the other end to form a communicating part 103, and while a part at the side of the discharge section 102 of the communicating part 103 is formed to be a centrifugal dehydrator section 104, the communicating part 103 between the supply section 101 and the centrifugal dehydrator section 104 is formed to be a hulling section 105, to which water adding means 106 is connected. The moisture conditioning device 108 communicates with the discharge section 102 of the hulling device 107 and moisture-conditions the polished rice discharged from the hulling device 107.

When polished rice is fed from the supply section 101 to the hulling section 105, water from the water adding means 106 is supplied to the hulling section 105, the amount of addition of water at this time is 5 to 20 weight % with respect to polished rice, preferably 15 weight % is added. The polished rice is transferred, stirred and hulled by screws 109, 110 and 111 inside the hulling section 105 with water. Consequently, rice bran adhering to the polished rice is separated in the water, hulling proceeds, and the hulling degree at this time is 0.5 to 2.0% with respect to the polished rice. The rice grains passing through the hulling section 105 are fed to the centrifugal dehydrator section 104 of the next step.

In the centrifugal dehydrator section 104, the rice grains and water are transferred further downward by the screw 112, and water containing rice bran powders and aleurone layers is discharged from a perforated wall 113. Next, the rice grains are discharged from the centrifugal dehydrator section 104 via the discharge section 102, and dried in the moisture conditioning device 108.

In the moisture conditioning device 108, the rice grains are spread on a net 114, and when they are moisture-conditioned and dried by being acted upon by draft action of wind, and have suitable water content, they are discharged from a rice discharge port 115 as non-bran rice products.

Meanwhile, explaining the non-bran rice production apparatus B (refer to Japanese Patent No. 3206752) with reference to FIG. 7, the non-bran rice production apparatus B includes a wet type processing section 200, a granular matter mixing section 201 and separation and dry section 202 from a top portion thereof in order. Polished rice passes through the wet type processing section 200, the granular matter mixing section 201 and the separation and dry section 202 in order, whereby it is finished to be non-bran rice with substantially no rice bran adhering to the rice grain surface.

When polished rice is thrown into a screw cylinder 204 connected to a supply cylinder 203 of a wet type processing section 200, mist water with rice grain weight ratio of about 5% is added from a spray port 205 situated near the supply cylinder 203, and they are transferred toward a transfer terminal side from a supplying screw blade 206 revolving at 500 rpm and stirred by an stirring blade 207. As a result of being stirred like this, mist water is uniformly attached to the rice grain surface, and rice bran in recessed portions on the rice grain surface is softened.

Next, in the granular matter mixing section 201, rice grains, which are supplied into a screw cylinder 210 of the granular matter mixing section 201 from a discharge port 208 of the wet type processing section 200 via a discharge cylinder 209, are transferred toward a transfer terminal side by a supplying screw blade 211 revolving at 600 rpm and an stirring blade 212 while being stirred, and in this situation, granular matters inside a granular matter supplying hopper 213 are supplied into the screw cylinder 210. The granular matters are formed, for example, by turning starchy matters such as tapiocas into alpha-starch and drying them, forming them into substantially a sphere shape with hardness of 2 to 5 $kgf/cm^2$, and granulating them into a fixed grain size smaller than the size of rice grain (for example, it is preferable to granulate them into a grain size of 1 mm to 1.7 mm) They are supplied at high temperature of 70° C. to 100° C. to be mixed with rice grains. The mixture ratio is about 50 weight % (weight ratio) with respect to the rice grains.

Bran powders and the like adhering to the polished rice, which absorb water in the previous step and is softened, are turned into alpha-starch at the moment when they contact granular matters at the high temperature, and are adsorbed by the granular matters and removed, and rice bran never adheres to the surface of the polished rice again. In this situation, latent heat of vaporization reduces the temperature of the rice grain surface.

In the separation and dry section 202, rice grains fed from the granular matter mixing section 201 via a discharge cylinder 214 are supplied into a screen cylinder 215 of the separation and dry section 202 for the final step, then transferred to a transfer terminal side by a supplying screw blade 216 revolving at 280 rpm and stirred by an stirring blade 217. In this situation, somewhat wet rice grain surfaces are dried by wind at about 40° C. flowing therein at 60 $m^3$ per minute from an air supply port 218, which makes separation from the granular matters easy at the same time.

The rice grains which has passed through the screen cylinder 215 are discharged outside the machine from a product discharge port 219, whereby they are finished to be non-bran rice in which rice bran in the recessed portions of the polished rice is completely removed.

The above-described methods are some examples of the production methods of non-bran rice that is an object to be measured. In order to find out the quality of the non-bran rice, in the present invention, non-bran rice is irradiated with excitation light and by utilizing the difference in the luminance of obtained self-emitted fluorescence, the quantitative proportion of each of the parts of the hull layer, aleurone layer and endosperm layer adhering to the grain surface is simultaneously identified to evaluate the quality.

Figure 1:
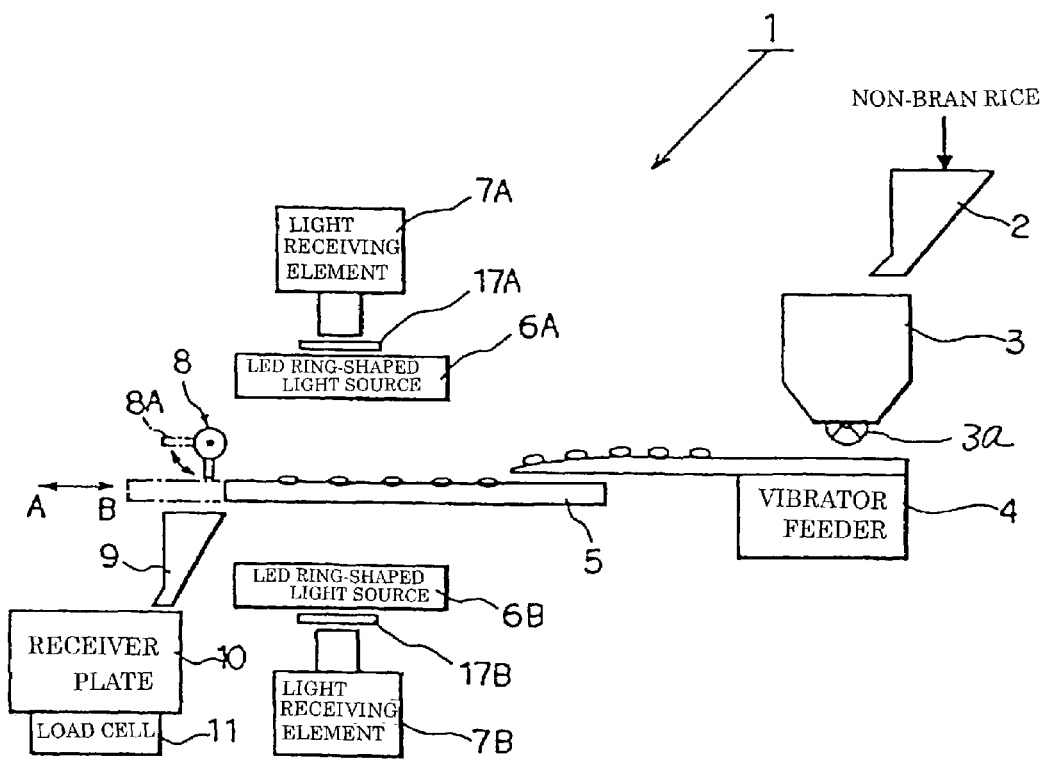
FIG. 1 is a schematic explanatory view of a quality evaluation apparatus for non-bran rice of the present invention.

FIG. 1 is a schematic explanatory view of the non-bran rice quality evaluation apparatus of the present invention. An evaluation apparatus 1 includes a hopper 2 for storing measurement objects, a tank 3 with a rotary valve 3a for taking out a predetermined amount of the measurement objects from the hopper 2, a vibrator feeder 4 for transferring the measurement objects from the tank 3 with rotary valve 3a by vibration, measurement object holding means 5 for aligning the measurement objects fed from the vibrator feeder 4 and holding them at a measurement position, excitation light source 6 (6A and 6B) which are located above and below the measurement object holding means 5 and irradiate the measurement objects with excitation light, light receiver means 7 (7A and 7B) which obtains luminance of self-emitted fluorescence obtained from transmission light or reflection light from the measurement objects, removing means 8 for scraping the aligned measurement objects from the measurement object holding means 5 to remove them, a hopper 9 for receiving the measurement objects removed by the removing means 8, a receiver plate 10 connected to the hopper 9 and a load cell 11 for measuring the measurement objects in the receiver plate 10.

Figure 2:
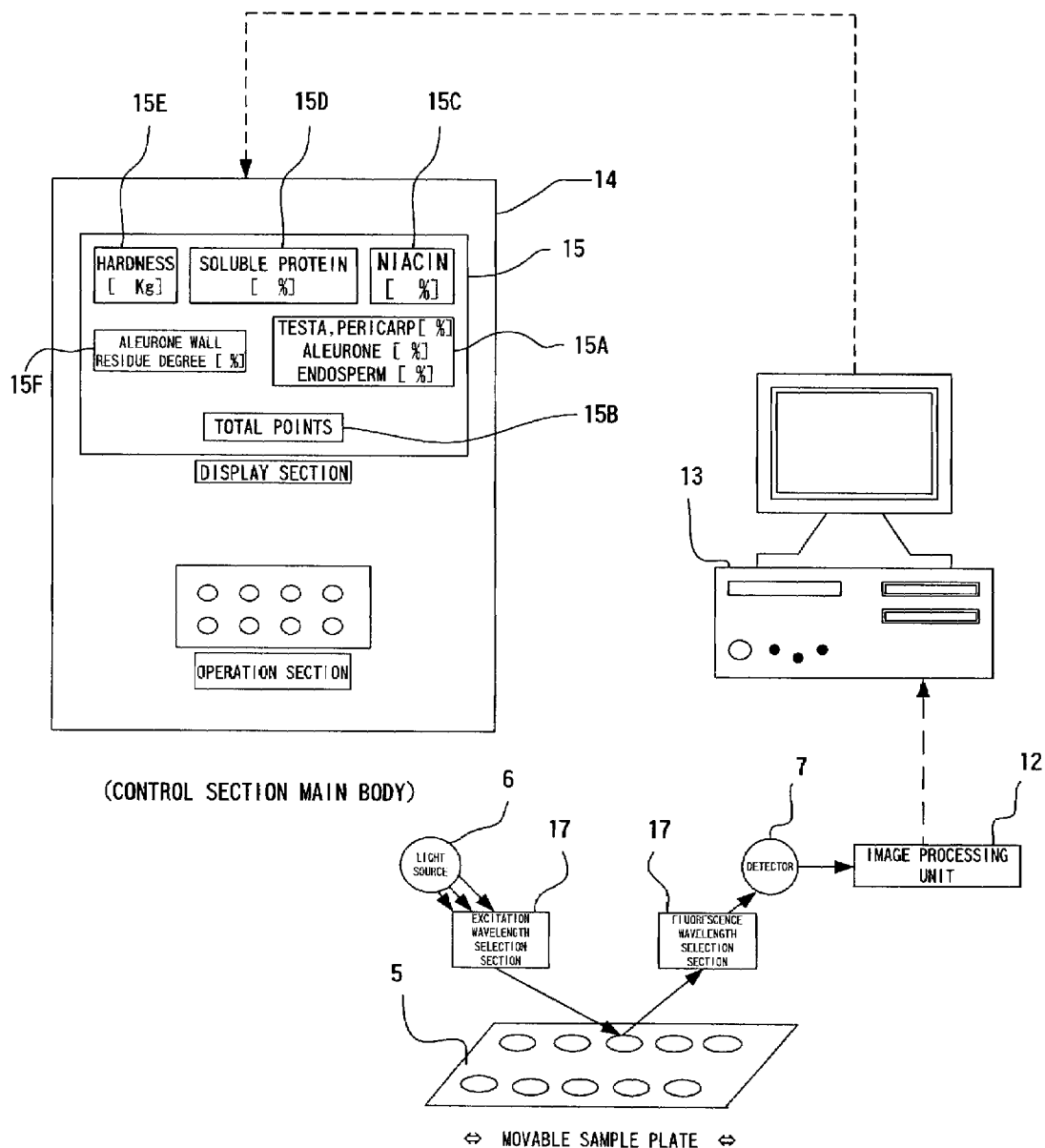
FIG. 2 is a schematic view showing connection of light receiver means, arithmetic operation and control means and display means.

Arithmetic operation and control means 13 is connected to the light receiver means 7 via an image processing unit 12 as shown in FIG. 2, and display means 14 is connected to the arithmetic operation and control means 13. In the arithmetic operation and control means 13, the quantitative proportion of each of the parts of the hull layer, aleurone layer and endosperm layer adhering to the surfaces of the measurement objects is calculated from the luminance of the obtained self-emitted fluorescence. The display means 14 includes a display device 15 for displaying the quality or taste value of the non-bran rice arithmetically operated in the arithmetic operation and control means 13. The display device 15 includes at least an ingredient display section 15A for displaying the proportion of each part of the hull layer part, aleurone layer part and endosperm layer part, and a quality evaluation display section 15B for displaying the quality or taste value of the non-bran rice in points or ranking. As the construction connectible to other ingredient measuring devices, a niacin ingredient display section 15C, a soluble protein ingredient display section 15D, a hardness display section 15E and an aleurone wall residue degree display part 15F may be provided.

Figure 3:
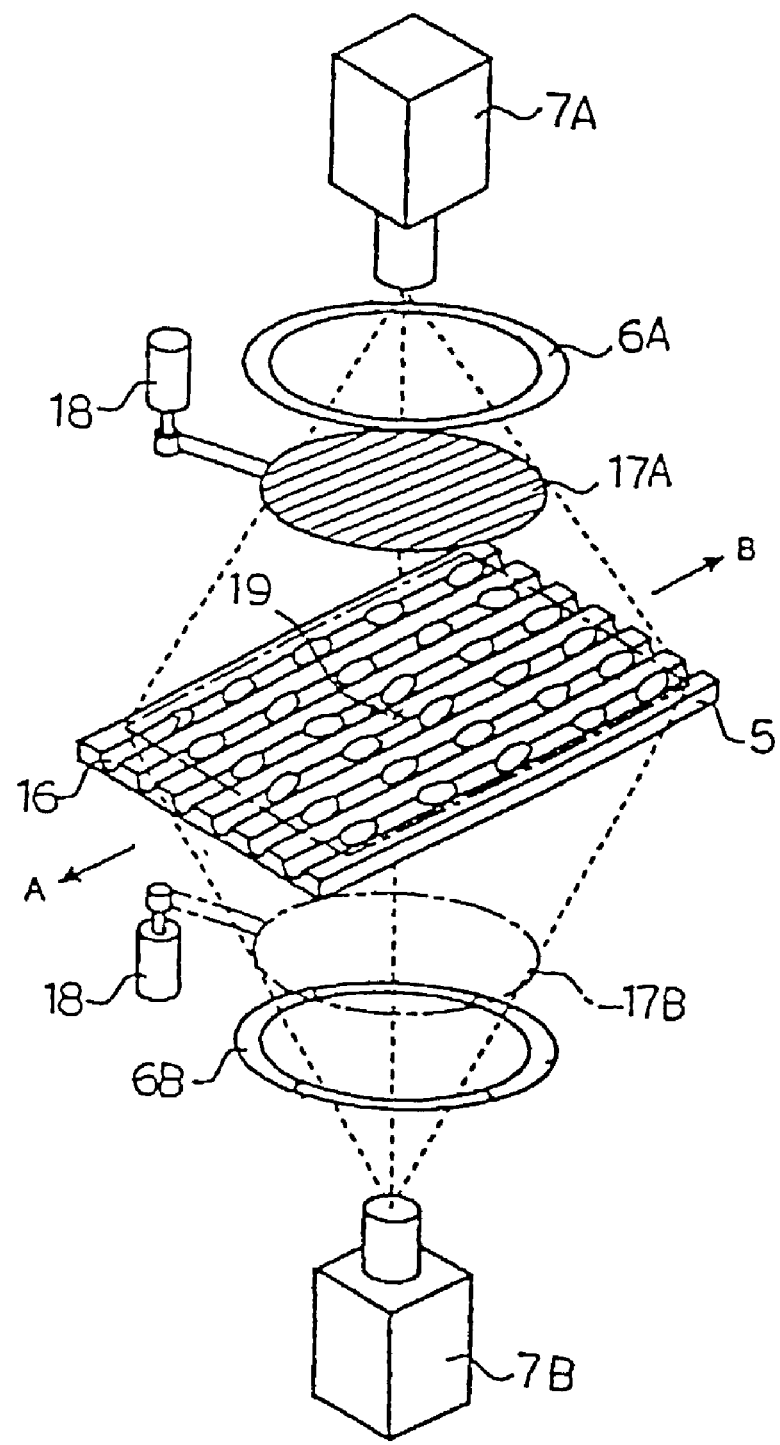
FIG. 3 is a schematic perspective view showing granular matter holding means and the light receiver means.

The configuration of the quality evaluation apparatus 1 will be further explained in detail with reference to FIG. 1 and FIG. 3. The measurement object holding means 5 has a slide plate structure for moving the measurement objects between a supply position, a measurement position 19, and discharge position in an A-direction or a B-direction shown in the drawings appropriately by means of a motor (not shown), and it is formed of a transparent material for transmitting light beams from the excitation light source 6, for example, a glass plate or an acrylic resin. A plurality of groove portions 16 are provided in a plurality of rows to align the measurement objects in a plurality of rows in a single layer state, which makes an obtained image clearer as compared with those promiscuously placed in disorder.

Reference numeral 17 denotes a filter provided between the light source 6 and the measurement object holding means 5, and by filtering the excitation light source 6 with the filter 17, it is made possible to irradiate a wavelength in the green range of about 560 to 570 nm as the excitation light. The filter 17 is rotatable by a motor 18 (see FIG. 3), and various kinds of filter 17 can be selected to be used.

The excitation light source 6 adopts an ordinary halogen lamp, tungsten lamp, xenon lamp or the like, and light beams thereof pass through the filter 17 and the wavelength in the green range of about 560 to 570 nm can be irradiated as excitation light, but such a lamp has a shorter service life, and also has the disadvantage of producing heat with large power consumption. On the other hand, it can be considered that the laser light with a large amount of light should be used as the excitation light source 6 to obtain a clear image, but this causes the disadvantage of requiring auxiliary devices and the like to make the cost higher. Considering the above, it is preferable to use light-emitting diode such as an LED which has a long service life with less power consumption, as the excitation light source 6. The light-emitting diode has the disadvantage of having a small amount of light, and in order to eliminate this, the light source, which is formed into a ring-shape constituted by a plurality of elements, is used in this embodiment (see FIG. 3). With such illumination, the entire surface of the measurement object holding means 5 can be irradiated without unevenness. If the light receiver means 7 is placed at a center portion of the LED ring-shaped light source 6, it becomes possible to obtain a clear image. The measurement object holding means 5 is formed of a transparent material, and for example, if the light source 6 and the light receiver means 7 are placed at an upper side and a lower side, a back portion (front portion) and a belly portion (reverse portion) of a rice grain can be measured, and more accurate quality evaluation can be performed.

As the light receiver means 7, it is preferable to use a CCD line sensor (or area sensor), a CMOS line sensor (or area sensor), which can instantly grasp a wide area, since it is necessary to identify each layer of the grain surface simultaneously according to the difference in the luminance of self-emitted fluorescence.

An operation of the above-described construction will be explained hereinafter. Non-bran rice being measurement objects is thrown from the hopper 2, the non-bran rice of an amount for measurement is taken out from the rotary valve 3a from the bottom part of the tank 3 with the rotary valve 3a, and the non-bran rice is transferred by the vibrator feeder 4 and is supplied to the measurement object holding means 5 while being aligned thereon. When the non-bran rice is supplied onto the measurement object holding means 5, the measurement object holding means 5 is transferred to the measurement position 19, and measurement is started.

The light beam from the excitation light source 6 passes through the filter 17 and the light beam of the wavelength in the green range of about 560 to 570 nm is irradiated to the non-bran rice as excitation light. As a result, the light receiver means 7 obtains the light beam of the wavelength in the red range of about 590 nm or more from the transmission light or reflection light from the non-bran rice as self-emitted fluorescence.

Figure 4:
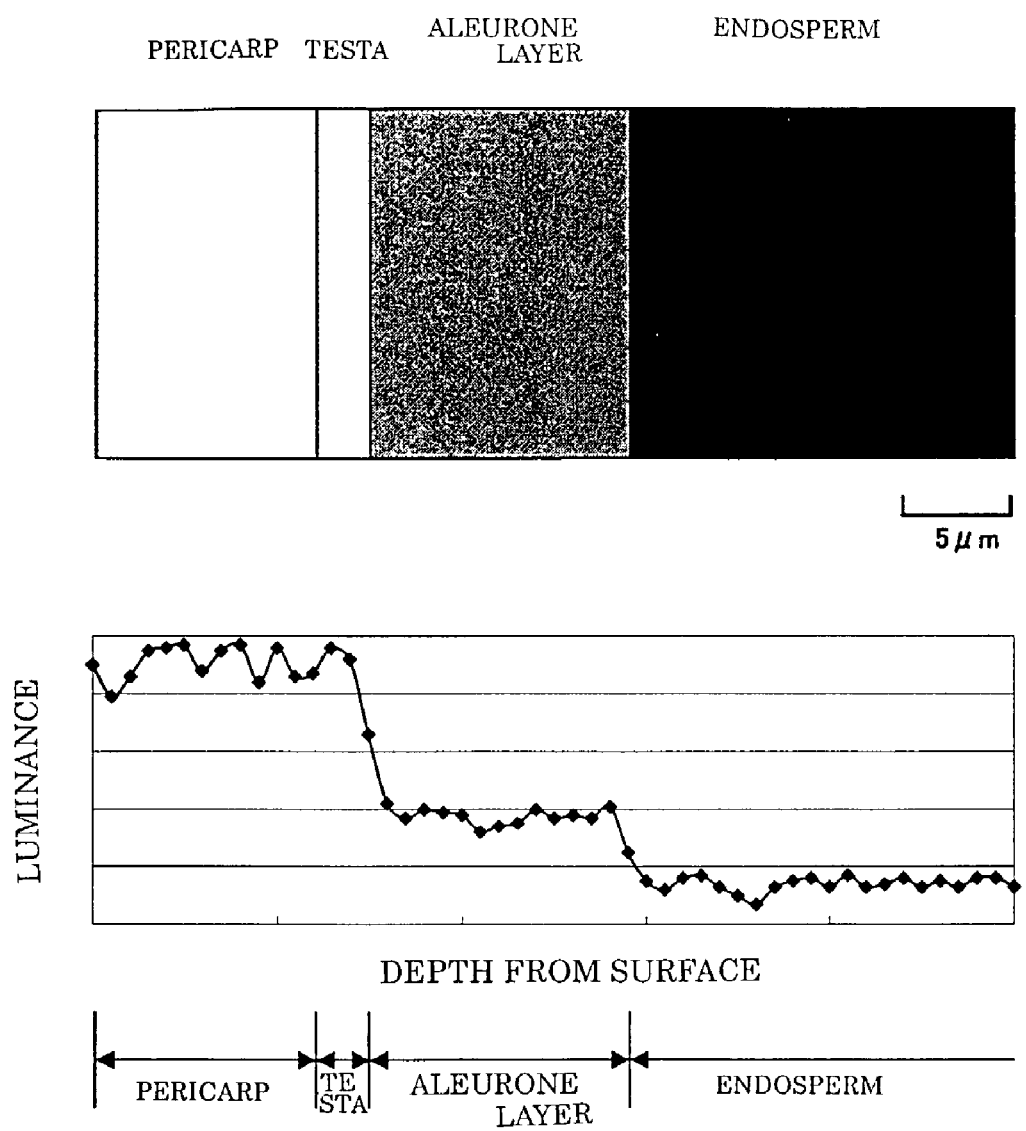
FIG. 4 is a diagram showing relationship between an inside state and luminance of a rice grain.

The light receiver means 7 receives self-emitted fluorescence obtained by irradiating the measurement objects with the excitation light, and the inside condition, as well as the surface condition, of the measurement objects can be optically evaluated, as compared with an apparatus which performs measurement with only reflection light or transmission light. For example, FIG. 4 is the diagram showing the relationship between the inside condition of the rice grain and the luminance, and thereby it is found out that the luminance of self-emitted fluorescence differs according to the depth from the surface of the rice grain. Referring to FIG. 4, the luminance of the Prichard layer and the test a layer (to about 12 $\mu$m) is in the range of about 40 to 50, the luminance of the aleurone layer (about 12 to 25 $\mu$m) is in the range of about 15 to 25, and the luminance of the endosperm layer (from about 25 $\mu$m) is in the range of about 5 to 10.

Figure 5:
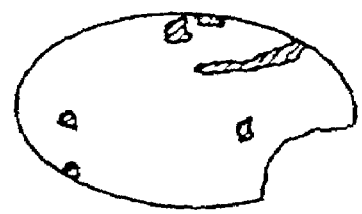
FIG. 5 is a view showing grouping of non-bran rice according to adherence proportions of a hull layer.
Figure 5:
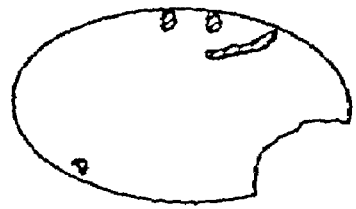
Figure 5:
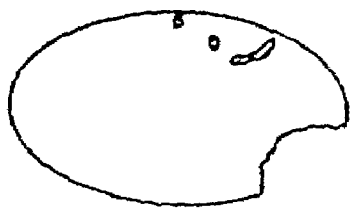

As described above, with the difference in the luminance of each layer as a reference, non-bran rice being the measurement objects is divided into groups to evaluate each quality. For example, FIG. 5 shows the adherence proportion of the hull layer, and according to the degree of processing of the non-bran rice, the non-bran rice is divided into three groups: A. lightly-processed non-bran rice which is cooked to be more delicious when the product is washed about twice to three times before being cooked, B. medium-processed non-bran rice which is cooked to be more delicious when the product is washed once before being cooked, and C. heavily-processed non-bran rice which can be cooked without washing the product before being cooked to evaluate the quality.

[Table 1]

Relationship between exposure proportion of rice grain surface and taste according to degree of processing of non-bran rice (The larger the number of "○" is, the larger the exposure proportion of the hull layer; the larger the number of "●" is, the larger the exposure proportion of the endosperm layer; and the larger the number of "◇" is, the better the taste)

|  | Polished rice | Non-bran rice Lightly processed type | Non-bran rice Medium processed type | Non-bran rice Heavily processed type |
|---|---|---|---|---|
| Hull layer (high luminance) | ○○○○○ | ○○○○ | ○○○ | ○○ |
| Endosperm layer (low luminance) | ●● | ●●● | ●●●● | ●●●●● |
| Taste value | ◇◇◇◇◇ | ◇◇ | ◇◇◇◇ | ◇◇◇ |

Table 1 shows the relationship between the exposure proportions of the rice grain surface and taste according to the degree of processing of non-bran rice. In case where the processing degree of the non-bran rice is light, the proportion of the high luminance is large, since a large amount of hull layer attaches thereto, and also the proportion of low luminance is small, since the exposure proportion of the endosperm layer is small. On the other hand, in case where the processing degree of the non-bran rice is heavy, the proportion of the high luminance is small, since a small amount of hull layer attaches thereto, and also the proportion of the low luminance is large, since the exposure proportion of the endosperm layer is large.

Meanwhile, concerning the processing degree of non-bran rice, the non-bran rice with heavy processing is not necessarily good in taste. When the rice grain of Table 1 is generally evaluated in the evaluation items such as outer appearance, flavor, taste, gluten, hardness and the like by the actual sensory test, it is found out that the taste value is better in order of polished rice, medium processed type of non-bran rice, heavily processed type of non-bran rice, lightly processed type of non-bran rice.

Accordingly, it is necessary in the detailed analysis of the taste evaluation for non-bran rice to grasp the processing degree of non-bran rice from the degree of luminance inputted into the arithmetic operation and control means 13 shown in FIG. 2 in association with the proportion of the respective components of the hull layer, aleurone layer and endosperm layer, and further to find a correlation between the processing degree of the non-bran rice thus grasped and the taste value previously stored in the sensory test or the like.

Each of the proportions of the hull layer, aleurone layer and endosperm layer of the non-bran rice as calculated above is displayed on the ingredient display section 15A in FIG. 2, and the quality such as the processing degree of non-bran rice and the taste value are displayed on the quality evaluation display section 15B which displays them in points or ranking.

After the quality of the non-bran rice is displayed by the display means 14 and a series of measurements is finished, the non-bran rice is removed from the measurement object holding means 5. Namely, the measurement object holding means 5 in FIG. 1 is moved in the A-direction, and when it is returned in the B-direction again, a projection part 8A of the removing means 8 is brought into contact with the measurement object holding means 5, and the aligned non-bran rice is scraped from the measurement object holding means 5 with the projection part 8A, whereby removal is carried out. The non-bran rice removed by the removing means 8 is received by the receiver plate 10 from the hopper 9. The non-bran rice in the receiver plate 10 is measured by the load cell 11. It is preferable to utilize the measured value which is inputted into the arithmetic operation and control means 13 for statistics on the quality of non-bran rice.

Examples will be shown hereinafter to further explain the present invention.

EXAMPLE 1

Quality evaluation was performed under the conditions of the excitation wavelength of 560 nm and fluorescence wavelength of 590 nm with use of eight kinds of samples of non-bran rice which is made by using Koshihikari of Niigata as sample unpolished rice, polishing it, and processing it according to the production methods of companies A, B, C, D, E, and F.

TABLE 2

|  | Non-bran rice (company A method) | Non-bran rice (company B method) | Non-bran rice (company C method) | Non-bran rice (company D method) | Non-bran rice (company E method) | Non-bran rice (company F method) |
|---|---|---|---|---|---|---|
| Hull layer (high luminance) | 6% | 2% | 18% | 33% | 21% | 17% |
| Aleurone layer (medium luminance) | 36% | 32% | 44% | 45% | 60% | 47% |
| Endosperm layer (low luminance) | 58% | 66% | 38% | 22% | 19% | 35% |
| Total | 100% | 100% | 100% | 100% | 100% | 100% |
| Taste value (ordinal rank) | 2 | 1 | 3 | 5 | 6 | 4 |

Conditions:
Breed of sample: Niigata Koshihikari
Excitation wavelenth: 560 nm (green)
Fluorescence wavelength: 590 nm (red)

As a result of the quality evaluation, the taste value of the non-bran rice by the method of the company B is ranked No. 1, that by the method of the company A is ranked No. 2, and that by the method of the company C is ranked No. 3, on the ground that the non-bran rice is poor in the hull layer and rich in the ablumen layer.

EXAMPLE 2

Hoshinoyume of Hokkaido was used as sample unpolished rice, and the quality evaluation was performed under the same conditions as in Example 1.

TABLE 3

|  | Non-bran rice (company A method) | Non-bran rice (company B method) | Non-bran rice (cnmpany C method) | Non-bran rice (company D method) | Non-bran rice (company E method) | Non-bran rice (company F method) |
|---|---|---|---|---|---|---|
| Hull layer (high luminance) | 12% | 5% | 12% | 44% | 34% | 33% |
| Aleurone layer (medium luminance) | 46% | 40% | 46% | 42% | 57% | 52% |
| Endosperm layer (low luminance) | 42% | 55% | 42% | 14% | 9% | 15% |
| Total | 100% | 100% | 100% | 100% | 100% | 100% |
| Taste value (ordinal rank) | 2 | 1 | 2 | 6 | 5 | 4 |

Conditions:
Breed of sample: Hokkaido Hoshinoyume
Excitation wavelenth: 560 nm (green)
Fluorescence wavelength: 590 nm (red)

As a result of the quality evaluation, the taste value of the non-bran rice by the method of the company B is ranked No. 1, and those by the methods of the company A and company C are ranked No. 2 with the same rate, on the ground that the non-bran rice is poor in the hull layer and rich in the ablumen layer.

According to the present invention, the method is for performing quality evaluation of non-bran rice product which is made by performing non-bran processing for polished rice after hulling, and the quality is evaluated by simultaneously identifying the quantitative proportion of each of the parts of the hull layer, aleurone layer and endosperm layer, each attaching to the surface, according to the difference in luminance of self-emitted fluorescence obtained by irradiating the measurement object with excitation light, and thus, concerning non-bran rice products made by performing non-bran processing of polished rice after hulling, it is made possible to identify the quantitative proportion of each of the parts of the hull layer, the aleurone layer and the endosperm layer, each attaching to the surface, at the same time, and divide the non-bran rice being the measurement object into three groups: the lightly-processed non-bran rice which is cooked to be more delicious when the product is washed about twice to three times before being cooked, the medium-processed non-bran rice which is cooked to be more delicious when the product is washed once before being cooked, and the heavily-processed non-bran rice which can be cooked without washing the product before being cooked to evaluate the quality.

The light used for quality evaluation of the measurement object is self-emitted fluorescence obtained by irradiating the measurement object with the excitation light, and therefore not only the surface condition of the measurement object but also the inside condition can be optically evaluated, as compared with an apparatus performing measurement with only reflection light or transmission light.

It is described above that the luminance obtained by irradiating the measurement object (rice) with the excitation light is about 40 to 50 for the hull layer, about 15 to 25 for aleurone layer, and 5 to 10 for the endosperm layer in the example in FIG. 4. However, if the luminance of the aleurone layer and the luminance of the endosperm layer are close to each other (closer than in the example shown in FIG. 4), it is difficult for the arithmetic operation and control means 13 shown in FIG. 2 to determine whether the self-emitted fluorescence inputted therein is the luminance of the aleurone layer or the luminance of the endosperm layer.

Thus, the quality of rice may be evaluated separately from a value (B) obtained by accurately measuring the proportion of the aleurone layer on the rice surface using the following method, a proportion (A) of the hull layer obtained by the arithmetic operation and control means 13 shown in FIG. 2, and a proportion (C) of the endosperm layer obtained by the calculation of 100−(A+B)=C.

[Measurement of an aleurone layer]

1. Store rice in a metal net.

2. Immerse the rice with the above-described net for five seconds in a beaker containing an organic solvent such as alcohols, acetone, and the like.

3. Take out the rice from the beaker and place it on a wiper and air-dry it. In this stage, the rice is degreased on its surface by the organic solvent, and the aleurone layer is whitened. However, the hull layer and endosperm layer of the rice keep the original color, and are not whitened.

4. Pick up the image of this rice with a color CCD camera, and by performing image processing, measure the area rate of the whitened parts distributed on the rice surface to obtain the ingredient proportion B of the aleurone layer.

As described above, according to the above-described method, by applying degreasing operation by the organic solvent to the rice surface, only the aleurone layer can be whitened. Namely, it is made possible to identify the aleurone layer and the other layers. Thus, by picking up the rice surface in the color image (or black-and-white image) and performing image processing, the area rate of the whitened part is measured, and the ingredient proportion of the aleurone layer can be obtained.

Further, the wavelength in the green range of about 560 to 570 nm is irradiated to the measurement object as the excitation light, and the wavelength in the red range of about 590 nm or more is obtained from the measurement object as the self-emitted fluorescence, and therefore the self-emitted fluorescence in the visible light ray range can be obtained, and the quantitative proportion of each of the parts of the hull layer, aleurone layer and endosperm layer, each attaching to the surface, can be grasped by visible observation by simple screen image means such as a monitor.

The quantitative proportion of each of the parts of the hull layer, aleurone layer and endosperm layer is simultaneously identified and displayed, and the taste of the non-bran rice is evaluated and displayed. Therefore, it is possible to analyze the taste evaluation for non-bran rice in detail from the correlation between the quantitative proportion of each of the parts and the sensory value such as a taste value.

The apparatus for performing the quality evaluation of the non-bran rice products includes the excitation light source for irradiating the measurement object with excitation light, the measurement object holding means for holding the measurement object at the measurement position, light receiver means for obtaining the luminance of the self-emitted fluorescence obtained from the transmission light or the reflection light from the measurement object, the arithmetic operation and control means for calculating the quantitative proportion of each of the parts of the hull layer, the aleurone layer and the endosperm layer, each attaching to the surface of the measurement object, and calculating the quality or the taste value of the non-bran rice, and the display means for displaying the value arithmetically operated in the arithmetic operation and control means, and therefore a quality evaluation apparatus for non-bran rice can be provided with a simple optical device.

Further, light-emitting diode is used as the excitation light source, and a CCD line sensor or a CMOS line sensor is used as the light receiver means, thus making it possible to provide a quality evaluation apparatus for non-bran rice with a compact and low-price optical device.

The light-emitting diode used as the excitation light source uses the ring-shaped light source composed of a plurality of elements, and therefore the excitation light can be irradiated to the whole of the measurement object held by the measurement object holding means, without unevenness.

The measurement object holding means has the slide plate structure which moves the measurement object to the supply position, the measurement position and the discharge position, it is formed of a transparent material which transmits the light beam from the excitation light source and is provided with a plurality of rows of the groove portions so as to align the measurement objects in a plurality of rows in a single layer state, thus making it possible to continuously perform supply of the measurement objects to the measurement object holding means, transfer to the measurement position and discharge of the measurement objects from the measurement object holding means, and the quality evaluation is more accurately performed by measuring the front and reverse portions of the measurement objects, and the measurement objects are aligned in the single layer state in which two of the objects do not overlap each other, thus making it possible to obtain the image more clearly.

Further, the display means includes the ingredient display section for displaying the proportion of each of the parts of the hull layer, aleurone layer and endosperm layer, and the quality evaluation display section for displaying the quality or the taste value of non-bran rice in points or ranking, and therefore as compared with the apparatus for displaying only the quality of non-bran rice, or the taste value in points or ranking, the quality evaluation of non-bran rice can be found out more precisely, since the proportion of each of the parts of the hull layer, aleurone layer and endosperm layer is displayed.

What is claimed is:

1. A quality evaluation method for non-bran rice for performing quality evaluation by simultaneously identifying a quantitative proportion of each of parts of a hull layer, an aleurone layer and an endosperm layer, which adhere to surfaces thereof, according to a difference in luminance of self-emitted fluorescence obtained by irradiating measurement objects with excitation light with a wavelength in a green range of about 560 nm to 570 nm and a wavelength in a red range of about 590 nm or more is obtained from said measurement objects as self-emitted fluorescence.

2. The quality evaluation method for the non-bran rice according to claim 1, wherein the luminance of said self-emitted fluorescence is obtained by utilizing transmission light or reflection light that is obtained by irradiating the measurement objects with the excitation light.

3. The quality evaluation method for the non-bran rice according to claim 1, wherein the quantitative proportion of each of the parts of said hull layer, aleurone layer and endosperm layer is simultaneously identified and taste of the non-bran rice is evaluated, results of which are displayed.

4. The quality evaluation method for non-bran rice according to claim 1, further comprising:
   obtaining an ingredient proportion of the aleurone layer comprising applying a degreasing operation using an organic solvent to the non-bran rice, picking up an image of the non-bran rice, and performing image processing;
   obtaining a quantitative proportion of the endosperm layer on the basis of the obtained quantitative proportions of the hull layer and the aleurone layer; and
   performing quality evaluation of the non-bran rice on the basis of the obtained quantitative proportions of the hull layer, aleurone layer and endosperm.

5. The quality evaluation method for the non-bran rice according to claim 1, wherein the excitation light has a same wavelength to identify the quantitative proportions of the hull layer, the aleurone layer and the endosperm layer.

6. A quality evaluation apparatus for non-bran rice for performing quality evaluation of non-bran rice products which are made by performing non-bran processing for polished rice after hulling, said apparatus comprising:
   an excitation light source for irradiating measurement objects with excitation light;
   measurement object holding means for holding the measurement objects at a measurement position;
   light receiver means for obtaining luminance of self-emitted fluorescence obtained from transmission light or reflection light from said measurement objects;
   arithmetic operation and control means for calculating a quantitative proportion of each of parts of a hull layer, an aleurone layer and an endosperm layer, which adhere to surfaces of said, measurement objects, according to the excitation light, and calculating quality or a taste value of the non-bran rice; and display means for displaying values arithmetically operated with the arithmetic operation and control means, the excitation light having a wavelength in a green range of about 560 nm to 570 nm, and a wavelength in a red range of about 590 nm or more is obtained from said measurement objects as self-emitted fluorescence.

7. The quality evaluation apparatus for the non-bran rice according to claim 6, wherein light-emitting diode is used as the excitation light source, and a CCD line sensor or a CMOS line sensor is used as the light receiver means.

8. The quality evaluation apparatus for the non-bran rice according to claim 7, wherein the light-emitting diode used as the excitation light source uses a ring-shaped light source comprising a plurality of elements.

9. The quality evaluation apparatus for the non-bran rice according to claim 6, wherein said measurement object holding means has a slide plate structure which moves the measurement objects to a supply position, the measurement position and a discharge position, said measurement object holding means is formed of a transparent material which transmits light beams from said excitation light source, and is provided with a plurality of rows of groove portions so as to align the measurement objects in a plurality of rows in a single layer state.

10. The quality evaluation apparatus for the non-bran rice according to claim 6, wherein said display means comprises an ingredient display section for displaying the proportion of each of the parts of the hull layer, the aleurone layer and the endosperm layer, and a quality evaluation display section for displaying the quality or the taste value of the non-bran rice in points or ranking.

11. A method for performing quality evaluation of non-bran rice made by performing non-bran processing for polished rice after hulling, comprising the steps of:

obtaining a quantitative proportion of a hull layer adhering to a surface according to luminance of self-emitted fluorescence obtained by irradiating said non-bran rice with excitation light;

obtaining ingredient proportion of an aleurone layer by picking up an image of said non-bran rice after performing degreasing operation by an organic solvent for said non-bran rice, and performing image processing;

obtaining a quantitative proportion of an endosperm layer based on said obtained quantitative proportions of the hull layer and the aleurone layer; and performing quality evaluation of the non-bran rice based on said obtained quantitative proportions of the hull layer, aleurone layer and endosperm layer.

* * * * *

UNITED STATES PATENT AND TRADEMARK OFFICE
CERTIFICATE OF CORRECTION

| | | |
|---|---|---|
| PATENT NO. | : 7,016,043 B2 | |
| APPLICATION NO. | : 10/270501 | |
| DATED | : March 21, 2006 | |
| INVENTOR(S) | : Takeshi Fukumori et al. | |

It is certified that error appears in the above-identified patent and that said Letters Patent is hereby corrected as shown below:

On Title PAGE, Item (56)
first page, column 2, FOREIGN PATENT DOCUMENTS, after "12/1992" insert
--G01N 21/85--
On Title PAGE, Item (56)
first page, column 2, FOREIGN PATENT DOCUMENTS, after "5/1993" insert
--G01N 21/27--
On Title PAGE, Item (56)
first page, column 2, FOREIGN PATENT DOCUMENTS, after "6/1993" insert
--G01N 21/35-- column 14, line 64 in claim 6, delete "said," and insert --said--

Signed and Sealed this

Twenty-second Day of August, 2006

JON W. DUDAS
*Director of the United States Patent and Trademark Office*